United States Patent [19]

Henry

[11] Patent Number: 5,679,325
[45] Date of Patent: *Oct. 21, 1997

[54] LIDOCAINE AEROSOL ANAESTHETIC

[76] Inventor: Richard A. Henry, 7 Toronto Street, Kingston, Ontario, Canada, K7L 4A3

[*] Notice: The term of this patent shall not extend beyond the expiration date of Pat. No. 5,593,661.

[21] Appl. No.: 718,182

[22] Filed: Sep. 19, 1996

Related U.S. Application Data

[63] Continuation of Ser. No. 405,930, Mar. 17, 1995, Pat. No. 5,593,661, which is a continuation of Ser. No. 216,476, Mar. 22, 1994, abandoned, which is a continuation-in-part of Ser. No. 38,930, Mar. 29, 1993, abandoned.

[51] Int. Cl.$^6$ .................................................. A61K 9/12
[52] U.S. Cl. .......................... 424/45; 514/626; 514/653; 514/817
[58] Field of Search ............................. 424/48; 514/626, 514/653, 817

[56] References Cited

U.S. PATENT DOCUMENTS 5,330,745  7/1994  McDow ................................ 424/45
5,534,242  7/1996  Henry .................................. 424/45
5,589,156  12/1996  Henry .................................. 424/45

FOREIGN PATENT DOCUMENTS 9200061  1/1992  WIPO .

Primary Examiner—Neil S. Levy
Attorney, Agent, or Firm—Whitham, Curtis, Whitham & McGinn

[57] ABSTRACT

The composition of the present invention combines the local anaesthetic lidocaine in free base form and the non-CFC aerosol propellant HFC-134a (1,1,1,2-tetrafluoroethane; $CF_3CH_2F$) or HFC-227 (1,1,1,2,3,3,3-Heptafluoropropane; ($CF_3CHFCF_3$), or a combination thereof, thus incorporating previously-unattainable amounts of the lidocaine free base in solution in a non-CFC aerosol propellant. This particular form of relatively-concentrated cosolvent-free anaesthetic permits improved inhalation delivery to the airway and lung, and topical airway local anaesthesia is thus readily provided. A method in accordance with the invention provides for release of the anaesthetic in aerosolized form of selected dosage from a canister containing the pressurized local anaesthetic composition into a patient's respiratory system directly or by way of an airway.

5 Claims, 1 Drawing Sheet

U.S. Patent  Oct. 21, 1997  5,679,325

LIDOCAINE AEROSOL ANAESTHETIC

CROSS REFERENCE TO RELATED APPLICATION

This application is a continuation of application Ser. No. 08/405,930 filed Mar. 17, 1995, U.S. Pat. No. 5,593,661 which was a continuation application of application Ser. No. 08/216,476 filed Mar. 22, 1994 now abandoned, which was a continuation-in-part of application Ser. No. 08/038,930, filed Mar. 29, 1993 now abandoned.

FIELD OF INVENTION

The present invention particularly concerns providing a local anaesthetic of aerosol form for topical airway anaesthesia and more particularly an aerosol dispensable composition of free base lidocaine and a suitable HFC propellant. The propellants are hydrofluorocarbon HFC-134a (1,1,1,2-tetrafluoroethane; $CF_3CH_2F$) and hydrofluorocarbon HFC-227 (1,1,1,2,3,3,3-Heptafluoropropane; $CF_3CHFCF_3$); or a combination thereof. The invention also relates to improvements in the delivery of such topical local anaesthetic to a human airway.

BACKGROUND OF INVENTION

Adverse physiological and neuromuscular response to laryngoscopy and intubation remains a significant problem of airway manipulation, both during anaesthesia and other airway diagnostic procedures. This is more fully discussed in the above-identified pending application the substance of which is incorporated hereby by reference thereto.

There is a need for an improved method of delivering a topical anaesthetic to a patient's airway and this is partly addressed by the aforementioned application. There further is need of a topical anaesthetic in suitable form for delivery into a patient's airway.

A known recommended procedure for airway anaesthetic administration is set forth in a text entitled "Clinical Anaesthesia" second edition edited by Paul G. Barash M.D. et al and published by J.B. Lippincott Company.

In this text it is indicated that "In airway anaesthesia manipulation of the airway either during laryngoscopy or during endotracheal intubation is often associated with laryngospasm, coughing, and undesirable cardiovascular reflexes. The anesthesiologist can abolish or blunt these reflexes by anaesthetizing one or all of the sensory pathways involved.

Airway anaesthesia can be performed by anaesthetizing one or all of the number of sensory distributions. Full anaesthesia will facilitate procedures such as nasal intubation or fiberoptic laryngoscopy.".

The procedure for airway anaesthetic administration described in the aforementioned text includes:

(1) nasal mucosal anaesthesia in which cotton pledgets soaked with anaesthetic solution are introduced through the nares. Contact time of "at least 2–3 minutes is required to allow adequate diffusion of the anaesthetic" which traditionally is "cocaine in a 4% solution". "Because of toxicity of cocaine and" "abuse problems" "alternate solutions have been recommended—primarily a mixture of 3–4% lidocaine and 0.25–0.5% phenylephrine".

(2) Topical anaesthesia to the posterior pharynx using a commercial spray while the nasal applicators are in place. It is indicated that "The inspiratory flow of gases should be enough to draw an anaesthetic solution into the posterior pharynx and even to the vocal cords themselves. If superior laryngeal nerve blockade has been performed prior to this, it is likely that the aerosol will be carried into the trachea itself. Again, a few minutes are needed for adequate onset of topical anaesthesia in the pharynx. Topical anaesthesia is less effective if there are copious secretions.".

(3) "Superior laryngeal nerve blockade, also performed while the nasal pledgets are in place", using a "5-ml syringe with a 1% lidocaine solution with a 23 gauge 1.75-cm needle". The aforementioned text indicates "blockade can be performed as part of total airway anaesthesia or it can be used independently to provide increased acceptance of indwelling endotracheal tubes in the intensive care unit".

(4) "Tracheal anaesthesia can be performed by a direct transcrycoid ("transtracheal") injection". The aforementioned text indicates "Not uncommonly, if the local anaesthetic is injected while the patient forcibly exhales it is possible to obtain adequate anaesthetic of the trachea, larynx, and posterior pharynx, without the need for either steps 2 or 3.".

(5) Lidocaine can be nebulized using a nebulizer driven by oxygen flow or airflow. The mist is breathed by the patient through an oxygen mask for 10–20 minutes. This will non-invasively topicalize the upper airway but is time consuming and requires patient co-operation.

The authors say that "Complications of these techniques are rare. Systemic toxicity from the local anesthetics is a distinct possibility because of the large quantities of drug required to produce sufficient mucosal anaesthesia". There is a caution that "if all four stages of airway anaesthesia are undertaken, the total milligram doses applied usually exceed the maximal recommended dose for peripheral injection. Fortunately, the mucosal absorption is less than the peripheral absorption, but close attention to the patient's mental status and preparation of treatment of toxicity are necessary.".

The techniques described in this text are used to facilitate manipulation of the airway of an awake patient. These procedures require considerable skill, patient co-operation and time to achieve the desired result. Because of these factors airway topicalization is routinely reserved for airway manipulations involving awake or lightly sedated patients. Topical airway anaesthetic would be beneficial in all anesthetized patients where intubation or airway manipulation is done. This, however, is not practical. Anaesthetic drugs including muscle relaxants are used to achieve the desired result. Topical lidocaine applied through the endotracheal tube of an intubated and ventilated patient will blunt the response to tracheal suctioning. This procedure is performed routinely and often hourly in these patients to clear airway secretions.

A topical lidocaine aerosol is currently available from Astra Canada and known as "Xylocaine Endotracheal Aerosol" but it requires direct application under vision, best achieved at laryngoscopy. The laryngoscopy is disadvantageously performed without prior airway topical anaesthesia. Intubation carried out at the time of laryngoscopy occurs too soon after the anaesthetic agent is applied for significant benefit to be achieved.

The known lidocaine aerosol has been implicated in inducing transient airway irritation and even laryngospasm. This preparation of lidocaine uses chlorofluorocarbon (CFC) propellants which are being discontinued to meet legal requirements.

For a topical anaesthetic to be effective, delivery direct to the site is required. The large droplet size produced by the aforementioned known Xylocaine Aerosol and the more basic spray delivery method necessitate direct application to the desired site. Drug delivery to the airway and lung can be achieved indirectly by the patient inspiring the aerosol if the droplet size is small enough. Large drops have a tendency to "rain out" or impact on surfaces, rather than follow gas flow around an obstructing surface. Therefore, delivery will be largely to the patient's nasal and oral mucus membranes. Particle size is an important factor in therapeutic aerosols and this along with other considerations are discussed in a text entitled "Pharmaceutical Inhalation Aerosol Technology" edited by A. J. Hickey and published by Marcel Dekker. On page 31 of this text, particle size is correlated with destination site. An aerosol particle diameter $\geq 10$ μm targets a deposition site of the oropharynx and $> 5$ μm the central airways.

In the art of aerosols, surfactants normally are used to ensure good dispersion of a powdered medicant and also provide for smooth operation of the valve through which the composition is dispensed. Conventional surfactants are sorbitan triolate and oleic acid. Solvents have also been used to increase the solubility of the surfactant in the propellant. CFC's have been conventionally used as propellants but these are gradually to be replaced by propellants that are more environmentally friendly. There are proposals for using HFC propellants, and in this regard reference may be made to PCT/GB91/01961 International Publication WO 92/08447 dated May 29, 1992; PCT/US91/07574 International Publication WO 92/06675 dated Apr. 30, 1992 and PCT/GB90/01454 International Publication WO 91/04011 published Apr.4, 1991. In these disclosures surfactants are required.

OBJECTS OF THE INVENTION

It is an object of the present invention to provide an improved lidocaine aerosol for delivery as a topical anaesthetic.

It is a further and principal object to provide a non-CFC aerosol lidocaine anaesthetic for topical application, particularly to the airway of a patient.

In keeping with the foregoing there is provided, in accordance with the present invention, an aerosol anaesthetic for topical airway anaesthesia using a non-CFC propellant in a dispensing canister adapted to release the anaesthetic in aerosolized form of preselected dosage. The anaesthetic is free base lidocaine and the propellant is HFC-134a, HFC-227, or a combination thereof.

Surprisingly, applicant herein has discovered that free base lidocaine is absorbed in sufficient therapeutic dosage in propellant HFC-134a and HFC-227 without the need of surfactants, solvents or the like.

Also, in accordance with a method of the invention, an oropharyngeal airway is inserted into the mouth of a patient according to current standard practice. Thereafter, the aforementioned anaesthetic in aerosolized form is released from the canister into the oropharyngeal airway, and thence into anaesthetizing contact with the patient's airway.

The anaesthetic of the present invention and application thereof may be used to provide reliable sensory block of the upper airway without direct vision of the anesthesiologist. Beneficially, this invention will improve lidocaine delivery by inhalation to facilitate manipulation of the airway of an awake patient, and will also facilitate smooth induction of anaesthesia by blunting the stress response to intubation. Intubation is routinely performed soon after induction, prior to surgery. A lighter plane of anaesthesia to achieve intubation may result and the need for muscle relaxation may be obviated, thus simplifying this critical period during general anaesthesia.

Superficial sensory block is rapid, typically onsetting within 5 to 30 seconds, with the block becoming more profound over a few minutes and affecting the pressure receptors deeper in the airway mucosal surface. By comparison, a nebulized mist of aerosolized lidocaine, actively inhaled, typically takes about ten to fifteen minutes to achieve delivery of the dose requirement, with only about 20% of the drug dose delivered to the patient. A preferred aerosol delivery device for carrying out the method includes a nozzle having an exit orifice adapted for fluid communication with the oropharyngeal airway. The delivery device may also include a valve stem seat of predetermined cross-sectional size and/or shape, for mating with a valve stem of likewise complementary cross-sectional size and/or shape.

SUMMARY OF THE INVENTION

What I claim to be my invention, then, comprises the following inter alia, alone or in combination:

An aerosol-dispensable topical anaesthetic composition suitable for inhalation administration into anaesthetizing contact with a patient's airway consisting essentially of lidocaine free base of the formula $C_{14}H_{22}N_2O$ dissolved in propellant 1,1,1,2-tetrafluoroethane of the formula $CF_3CH_2F$ or 1,1,1,2,3,3,3-heptafluoropropane of the formula $CF_3CHFCF_3$, or a combination thereof, the percentage of lidocaine free base by weight of the composition being at least 1% and the lidocaine free base aerosol droplets having a particle size between 5 and 25 microns; such an aerosol-dispensable topical anaesthetic composition under pressure in a metered dosage-dispensing container; such an aerosol-dispensable topical anaesthetic composition wherein the lidocaine free base aerosol droplet particle size is 5 to 10 microns; such an aerosol-dispensable composition containing no solvent other than propellant; such an aerosol-dispensable anaesthetic wherein a metered dosage dispensed by the metered dosage-dispensing container is in the range of 5 to 20 mg of lidocaine free base per dose; such an aerosol-dispensable anaesthetic composition wherein the concentration of the lidocaine free base is greater than 3% by weight of the composition; such an aerosol-dispensable anaesthetic composition wherein the concentration of the lidocaine free base is greater than 5% by weight of the composition; such an aerosol-dispensable anaesthetic composition wherein the concentration of the lidocaine free base is approximately 5–15% by weight; such an aerosol-dispensable anaesthetic composition wherein said concentration is greater than 10 mg/ml and up to about 759 mg/ml; such an aerosol-dispensable anaesthetic wherein a metered dose dispensed by the metered-dose-dispensing container is up to about 100 microliters; such an aerosol anaesthetic wherein the concentration of the lidocaine free base provides at least 5 mg of lidocaine free base per metered dosage; such an aerosol-dispensable anaesthetic composition wherein the concentration of the lidocaine free base provides 5–20 mg of lidocaine free base per metered dosage; such an inhalation aerosol-dispensable topical anaesthetic composition in aerosol form consisting essentially of lidocaine free base of the formula $C_{14}H_{22}N_2O$ dissolved in propellant $CF_3CH_2F$ or $CF_3CHFCF_3$, or a combination thereof, under pressure in a metered-dosage dispenser, the percentage of lidocaine free base by weight of the composition being at least 5% and the lidocaine free base aerosol droplets having a particle size between 5 and 25 microns; such an inhalation aerosol-dispensable topical anaesthetic composition wherein the percentage of lidocaine free base by weight of the composition is 5 to 15%; and such an aerosol-dispensable topical anaesthetic composition wherein the lidocaine free base aerosol droplet particle size is 5 to 10 microns.

BRIEF DESCRIPTION OF THE DRAWINGS

The invention, in part, is illustrated by way of example with reference to the accompanying drawings wherein.

DESCRIPTION OF PREFERRED EMBODIMENT

Figure 1:
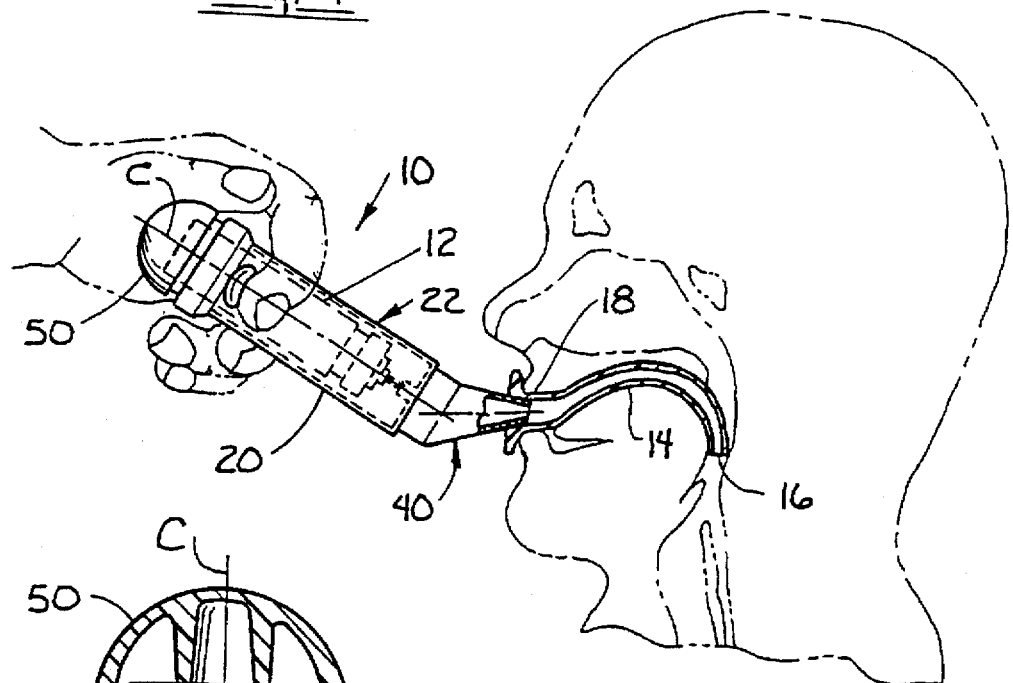
FIG. 1 is a perspective view of an apparatus for use in delivery of the topical aerosol anaesthetic of the present invention to a patient.

Referring to the drawings, illustrated is a pressurized aerosol containing an anaesthetic of the present invention and an apparatus 10 for delivering such anaesthetic to the airway of a patient. Shown in the drawing is an aerosol dosage dispensing container 12 containing a topical anaesthetic and propellant, to be further described hereinafter, in fluid communication with an oropharyngeal airway 14, depicted as disposed within the oropharyngeal cavity, represented by a dotted line, of a patient who is lying down.

As can be understood from FIG. 1, an oropharyngeal airway extends from the lips to the pharynx, and has a curved shape that fits over the tongue and an orifice 16 that "looks" straight at the larynx and trachea.

Figure 2:
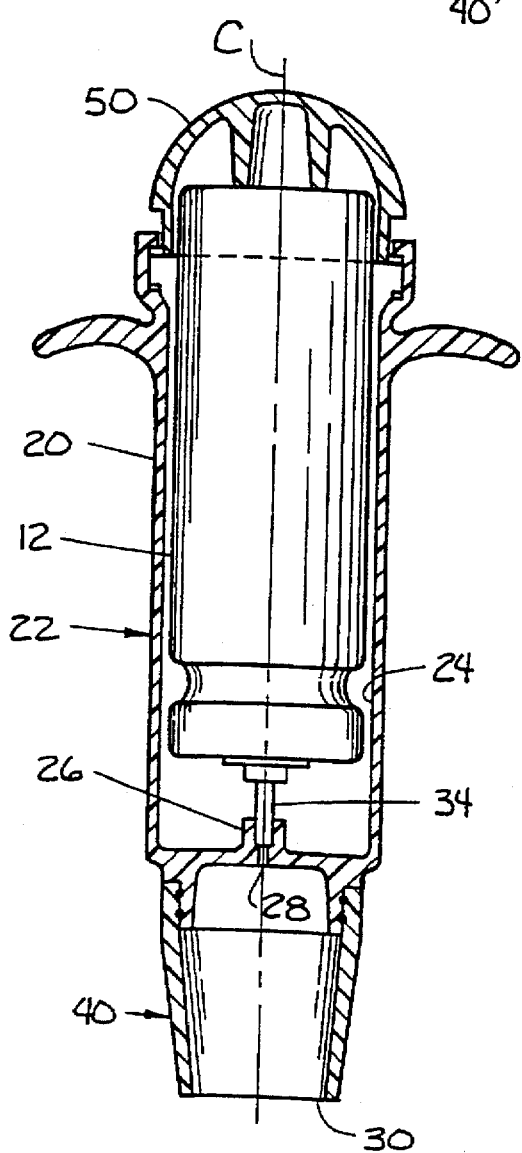
FIG. 2 is a cross-sectional view of the aerosol delivery device of FIG. 1, taken substantially along the longitudinal axis thereof.

In FIG. 2, there is illustrated a casing or housing 20 of an aerosol delivery device 22 which has a cavity 24 removably receiving the aerosol canister 12. There is a valve stem seat 26 with an aperture 28 that communicates with an exit orifice 30 of the delivery device. The exit orifice is designed for fluid communication with entrance 18 to airway 14 (see FIG. 1).

Canister 12, generally constructed as is conventional in the aerosol art, has a tubular valve stem or spray head 34. The valve stem is seated within valve stem seat 26, and has an outlet orifice situated for directing an aerosol discharge through aperture 28. Pressing the valve stem inwardly of the canister causes a metered dose of aerosolized anaesthetic to be released from a pre-filled metering chamber (not shown) and to issue from the canister orifice. To accomplish this, casing 22 has a removable case closure 50 mounted on the casing for reciprocal movement within defined limits. The cap engages the bottom end of the canister 12.

The valve stem 34 of the topical anaesthetic-containing canister has a selected shape, for instance a triangular cross-sectional shape, and the valve stem seat has a complementary configuration. In this way, use of the delivery device may be restricted to a topical anaesthetic for predetermined usage and/or dosage by correlation thereof to different shapes or sizes so as to avoid a potential drug overdose, i.e., child vs. adult.

A nozzle 40 is preferably removably attached to casing 20 and terminates in the above-mentioned exit orifice 30. Advantageously, as shown in FIG. 1, the nozzle 40 is shaped to direct the expelled aerosol at an angle with respect to a main or longitudinal axis C of the casing, so as to facilitate operator use in not requiring direct alignment. The exit orifice 30 end of the aerosol delivery device 22 is suitably sized and shaped for insertion into the entrance portion of an airway device 14.

The anaesthetic of the present invention for topical airway anaesthesia is free base lidocaine and the selected non-CFC propellant $CF_3CH_2F$ or $CF_3CHFCF_3$ or a combination thereof in a predetermined dosage delivery container 12. An appropriate concentration of the anaesthetic is in container 12. Preferably about 1-20 wt.% lidocaine free base is typically selected to provide about 2 to 20 mg of lidocaine free base per metered dose.

In preparing an aerosol anaesthetic of the present invention lidocaine was obtained from Spectrum Chemical Mfg. Corporation, 14422 S. San Pedro St., Gardena, Calif. 90428 and labelled, Lidocaine U.S.P./N.F. CAS 137-58-6. The formula is given as $C_{14}H_{22}N_2O$, F.W. 234.34. This form of lidocaine is the free base and not the hydrochloride salt. The solubility of lidocaine was measured in several aerosol propellants by weighing a known amount of the lidocaine into a glass aerosol bottle and then gradually adding propellant until the lidocaine went into solution. This procedure gave an approximate solubility of lidocaine in each of the propellants.

The aerosol propellants tested were HFC-134a, available from E.I. du Pont de Nemours and Company under their Trademark Dymel® 134a ($CF_3CH_2F$), and HFC-227, supplied by Great Lakes Chemical under their Trademark FM 200, and provided outstanding lidocaine solubility, both in percent by weight and even more importantly in mg/ml of the propellant.

The results are presented below.

| Solubility of Lidocaine in Selected Propellants | | |
|---|---|---|
| | Solubility | |
| Propellant | Weight | mg/ml |
| Dymel® 134a $CF_3CH_2F$ | 58 | 759 |
| FM 200® $CF_3CHFCF_3$ | 45 | 602 |
| Water | Ins. | — |

The propellant Dymel® 134a (HFC-134a; 1,1,1,2-tetrafluoroethane) is a nonflammable vapor at room temperature and atmospheric pressure. Certain of its physical properties, e.g., vapor pressure, are very close to those of CFC-12. Its chemical formula is $CF_3CH_2F$.

Further information is available in technical information bulletin H-44691 (September 1992) of E.I. du Pont de Nemours and Company entitled "Dymel aerosol propellants information".

The propellants Dymel® 134a ($CF_3CH_2F$) and FM 200® ($CF_3CHFCF_3$) are aerosol propellants containing no chlorine atoms and, as such, fall completely outside concerns about stratospheric ozone destruction by chlorofluorocarbons or other chlorinated hydrocarbons. For example, HFC-134a has an Ozone Depletion Potential of 0.00 and the U.S. Environmental Protection Agency has found it is not a Volatile Organic Compound (VOC), i.e., it has negligible photochemical reactivity (55 FR 11418). It can be used alone or mixed with propellant HFC-227.

The foregoing Examples can readily provide a dosage of roughly 60–75 mg of lidocaine per 100 microliters of the combined dispensed aerosol. Less concentrated solutions are, however, preferred for topical airway anaesthesia, e.g., providing 2–20 mg of lidocaine per 50 microliters of combined dispensed aerosol.

The particle size of the aerosol of the present invention is preferably in the range of 5 to 10 μm to target a deposition site of the oropharynx and central airways (tracheobronchial). Particle sizes in the range of 5 to 25 microns are considered acceptable.

In summary, in the inhalation aerosol-dispensable topical anaesthetic composition of the invention, due to its unpredictably great solubility in the selected propellant, the lidocaine free base can be present in an amount of 1 to 10% by weight, advantageously 3 to 6% by weight, thus for example to provide a metered inhalation dose of about 5–20 mg per metered dose of 100 microliters, that is, at least 5 mg per 100 microliters of the dispensed aerosol composition, and is frequently and advantageously present in the composition in an amount of about 5% by weight and on the order of at least about 10 mg/ml of the composition. One percent by weight gives 10 mg of lidocaine free base per ml of composition.

In a broader sense, the present invention provides: an aerosol-dispensable topical anaesthetic composition suitable for inhalation administration as described in the foregoing wherein the percentage of lidocaine free base by weight of the composition is at least 1% and preferably wherein the lidocaine free base aerosol droplets produced have a particle size between 5 and 25 microns, preferably 5–10 microns, and such aerosol-dispensable topical anaesthetic composition under pressure in a metered dosage-dispensing container and wherein the composition contains no solvent other than the propellant(s). The metered dosage dispensed by the metered dosage-dispensing container may be in the range of 5–20 mg of lidocaine free base per dose, and the concentration of the lidocaine free base in the composition is preferably greater than 3% by weight of the composition, at least 5% by weight and preferably greater than 5% by weight of the composition, and most preferably approximately 5–15% by weight of the composition. As to the concentration of lidocaine free base in the composition, it is greater than 10 mg/ml and may even be as great as about 759 mg/ml, which is the limit of solubility of the lidocaine free base in the most advantageous propellant of the invention. As to the metered dose dispensed by the metered dosage-dispensing container, it may be 25, 50, or up to about 100 microliters per metered dose, and the metered dose should provide at least 5 mg of lidocaine free base per metered dosage, preferably about 5–20 mg of lidocaine free base per metered dosage, and various combinations of the foregoing characteristics, amounts, and concentrations will be immediately apparent to one skilled in the art. For example, in the inhalation aerosol-dispensable topical anaesthetic composition of the invention, the lidocaine free base may be present in an amount of 2–58% by weight, advantageously 5–15% by weight, thus to provide a metered inhalation dose of about 2–39 mg (frequently about 5 mg and preferably about 10 mg) per metered dose of 50 microliters of the dispensed aerosol composition, and may advantageously be present in the composition in an amount of about 15% by weight and on the order of about 200 mg/ml of the composition.

I claim:

1. An aerosol dispensable solution consisting essentially of at least one percent by weight lidocaine free base dissolved in a hydrofluorocarbon propellant selected from the group consisting of 1,1,1,2-tetrafluoroethane and 1,1,1,2,3,3,3-heptafluropropane and combinations thereof without the presence of a solvent other than said hydrofluorocarbon propellant and without the presence of a surfactant.

2. The solution of claim 1, wherein the propellant is 1,1,1,2-tetrafluoroethane.

3. The solution of claim 1, wherein the propellant is 1,1,1,2,3,3,3-heptafluoropropane.

4. The solution of claim 2, wherein the lidocaine free base is soluble in the propellant up to about 58 weight percent and about 759 mg/ml.

5. The solution of claim 3, wherein the lidocaine free base is soluble in the propellant up to about 45 weight percent and about 602 mg/ml.

* * * * *